United States Patent [19]

Tiedeman et al.

[11] Patent Number: 4,828,890
[45] Date of Patent: May 9, 1989

[54] METHOD FOR INCREASING BLEED RESISTANCE OF PRESERVED PLANTS AND PRODUCTS OF THE METHOD

[75] Inventors: George T. Tiedeman, Seattle; David W. Park, Puyallup; Robert H. Young, Maple Valley, all of Wash.

[73] Assignee: Weyerhaeuser Company, Tacoma, Wash.

[21] Appl. No.: 182,674

[22] Filed: Apr. 18, 1988

[51] Int. Cl.[4] .................. A01G 5/06; A01N 3/00; A41G 1/00
[52] U.S. Cl. ............................................ 428/22; 427/4
[58] Field of Search ............................. 427/4; 428/22

[56] References Cited

U.S. PATENT DOCUMENTS

| | | |
|---|---|---|
| 1,410,226 | 3/1922 | Segall . |
| 1,484,656 | 2/1924 | Koroff et al. . |
| 1,714,838 | 5/1929 | Anderson . |
| 1,908,922 | 5/1933 | Ruzicka . |
| 2,026,873 | 1/1936 | Dux ............................................ 99/1 |
| 2,978,348 | 4/1961 | Fessenden .............................. 117/3 |
| 3,895,140 | 7/1975 | Sheldon et al. ........................ 428/22 |
| 4,243,693 | 1/1981 | Nordh .................................... 427/4 |
| 4,278,715 | 7/1981 | Romero Sierra et al. ............. 428/22 |
| 4,287,222 | 9/1981 | Robinson ................................ 427/4 |
| 4,328,256 | 5/1982 | Romero-Sierra et al. ............. 427/4 |
| 4,664,956 | 5/1987 | Dukkehul et al. .................... 428/22 |
| 4,710,394 | 12/1987 | Sellegaard ............................. 427/4 |

FOREIGN PATENT DOCUMENTS 1542903  1/1966  Fed. Rep. of Germany .
2160310  11/1971  France .

Primary Examiner—Michael Lusignal

[57] ABSTRACT

The present invention is a method of preserving plants which achieves reduced bleeding of the preservative material when the plants are subjected to elevated humidity conditions. The method comprises perfusing the plants with an aqueous preservative composition in which the preservative is primarily an alkylene oxide oligomer, 1,3-butanediol, or 1,4-butanediol. Preferred alkylene oxide oligomers are di- and polyethylene glycols in the molecular weight range of about 200–1500 and di- and polypropylene glycols with an average molecular weight below about 450. The preferred materials may be used with lesser amounts of secondary humectant materials selected from glycerol, ethylene glycol, propylene glycol, magnesium chloride or magnesium bromide hexahydrate, and water soluble cycle phosphonate esters. Plants are conventionally treated by perfusing an aqeous treatment solution into the vascular system through a cut stem or other incision which exposes the xylem. Treatment is carried out at a temperature in the range of 20°–50° C. at a relative humidity in the range of about 20%–80% for a period time up to about 14 days.

14 Claims, 2 Drawing Sheets

METHOD FOR INCREASING BLEED RESISTANCE OF PRESERVED PLANTS AND PRODUCTS OF THE METHOD

BACKGROUND OF THE INVENTION

The present invention is directed to a method for preserving plants and plant parts using new preservative materials that reduce bleeding of the preservatives when the preserved plants are subjected to high humidity conditions. The invention is also directed to the preserved plants produced by the method.

In recent years a significant new industry has sprung up based on improved technology for preserving plants. These processes give very high quality, natural appearing products. Preserved plants are used in environments that might be marginal or unsuitable for living plants, or where the care and maintenance of living plants would be too costly or impractical. A wide number of different types of plants have been offered to date. These vary from floral arrangements, to small foliage-type shrubs, all the way to small trees up to about 6-7 meters high.

In one process, the plants are cut above the root line and the stem is immersed in a treating solution which is perfused into the plant by natural fluid transport processes. Environmental temperature and humidity are carefully controlled during the treatment time, which can last up to two weeks. Glycerol is almost universally used as the preservative material, along with minor amounts of salts for osmolality and/or pH control, and water soluble dyes.

The processes outlined in Nordh, U.S. Pat. No. 4,243,693, can be said to be typical of the present state of the art. Nordh describes an aqueous preservative solution having from 18-35% by volume of glycerol and 2-10 g/L of the yellow food dye tartrazine. The dye is said to be a critical component of the composition if optimum preservation is to be obtained. The solution also contains 1-15 g/L of $KNO_3$ as well as minor amounts of a blue dye to produce a preferred green color. Treatment of the plants is carried out in an environment in the range of 15°-33° C. in air which is at most no greater than 60% relative humidity.

Sellegaard, in U.S. Pat. No. 4,710,394, teaches a very similar preservative system to that described by Nordh. The exception is the inclusion of 1-6% of an organic acid, preferably citric acid, in the preservative solution. One other difference is his use of a treatment temperature range for some products well above that described by Nordh as being critical. A major claim to novelty by Sellegaard is that the dry chemicals in his mixture are packaged separately and combined with glycerine and water at the point of use.

Reference is made here to an earlier application commonly assigned with the present one. This describes treatments which produce flame retardant plants, especially useful in public places where fire hazard must be kept to an absolute minimum. This application, Ser. No. 113,312, filed Oct. 28, 1987, is hereby incorporated by reference.

In addition to the process of perfusion, a number of inventors have taught immersion of the entire plant being treated in a bath containing glycerine as the principal preservative. These include Segall, U.S. Pat. No. 1,410,226, who directs his process to the preservation of ferns. These are first treated in a caustic solution, bleached, and then dyed by immersion in a warm solution of dye, glycerine, alcohol, and water.

In U.S. Pat. No. 1,484,656, to Koroff et al., the plants are first dried and then placed in a preserving solution of glycerine, water, and formalin.

Dux, in U.S. Pat. No. 2,026,873, describes a preservative solution containing glycerine, a vegetable gum, sodium benzoate, and water soluble sulfonated vegetable oil. In contrast to most of the other processes, Dux submerges his plants for only a few minutes whereas the other processes described to this point need many hours or days.

U.S. Pat. No. 3,895,140, to Sheldon et al, teaches preservation of cult foliage by immersing it in a relatively hot solution of glycerine or polyglycerine at temperatures in the range of 60°-82° C. or even higher. The inventors note that a number of other polyols including trimethylolpropane, propylene glycol, sorbitol and pentaerythrytol were not effective as preservative materials.

Romero-Sierra et al, in U.S. Pat. No. 4,278,715 and 4,328,256, describe a very complex mixture and process for preserving plant specimens. The treatment solutions contain a diol or triol such as ethylene glycol or glycerine but also require many other materials, including a lower carboxylic acid as a preservative. The main advantage taught by these inventors is that the natural green color is preserved. However, it is apparent that the specimen is usable only for a period of a few weeks without additional treatment. To get permanent preservation, this second treatment involves immersion in a solution of 100-700 mL of glycerine per liter for a period two to three weeks, or even permanently, at ambient conditions.

French Pat. No. 2,160,310 teaches preservation of cut foliage by immersion in a solution containing one third glycerine and two-thirds water.

A number of other patents might be cited in which a polyol preservative is either not required or is present as an optional ingredient. These include U.S. Pat. No. 1,714,838 to Anderson, which describes the use of calcium chloride as a plant preservative.

Ruzicka, in U.S. Pat. No. 1,908,922, describes treatment with a sucrose solution for extending the life of cut flowers. This inventor makes no claim to permanent preservation, however.

Fessenden, in U.S. Pat. No. 2,978,348, teaches preservation by immersing foliage in a solution which includes a water soluble salt of aluminum, an alkaline salt of an acid which will form insoluble salts of aluminum under alkaline conditions, and a volatile organic acid to reduce the pH until the plant is withdrawn from the treating solution. The solution may contain a humectant which is a neutral salt of an aliphatic amine or it may optionally include polyols such as glycerol, sorbitol, or polyethylene glycol 200. The polyols appear to be an optional and a minor part of the formulation and their specific function or purpose is not disclosed.

Along with the increased popularity of preserved plants a problem has now been recognized which, until the present time, has not been dealt with in the related literature. This is the matter of bleeding of the preservative materials from the leaves and stems of the treated plant. Ordinarily this is not a serious problem. However, it may become one after the plant is exposed for protracted periods in which the humidity is very high. Very high humidity is a common summer condition in the eastern and Gulf Coast portions of the United States and in other areas of the world. The bleeding is unsightly because it gives the affected portions a wet, sticky appearance and may encourage the growth of molds or fungi. In some cases bleeding may become so severe that droplets of preservative actually fall from the plant onto the floor. These droplets carry with them the water soluble dyes used for control of foliage color. Permanent staining of carpets or other flooring material has occasionally resulted during these extreme bleeding situations.

The present invention deals with treatment methods and new preservative materials which greatly reduce or completely overcome the problem of bleeding, even after relatively prolonged exposure to high humidity conditions.

SUMMARY OF THE INVENTION

This invention is a method of preserving plants which assures excellent overall quality of the ultimate product. The method is particularly beneficial since it achieves reduced exudation or bleeding of preservative materials when the preserved plants are subjected to elevated humidity conditions for relatively long periods of time. The invention involves perfusing into living plants an aqueous preservative composition comprising a sufficient amount of a primary hydrophilic humectant/preservative material. The most preferred humectant/preservative chemicals are new in the present application. They are selected from alkylene oxide oligomers, 1,3-butanediol, 1,4-butanediol, or mixtures thereof with each other or with minor amounts of a secondary humectant material. The secondary humectant is selected from chemicals which are known in the past to be useful plant perservatives. These include glycerol, ethylene glycol, propylene glycol, magnesium chloride or magnesium bromide hexahydrate, and water soluble cyclic phosphonate esters.

The word "perfuse" is used in the context of diffusing a liquid material substantially uniformly at least within the plant's active xylem and foliage.

By "living plant" is meant that the plant or plant part must be physiologically active; i.e., it must be capable of imbibing and transporting aqueous liquids at least through the xylem into the foliage.

By "minor amount" is meant that the secondary humectant material is present in a concentration lower tha the concentration of primary humectant material. Stated otherwise, the secondary humectant comprises less than half of the active humectant/preservative materials present in the treating solution.

By "humectant/preservative" is meant a material which will replace a portion of the water and original electrolytes present in the plant cells so that the foliage and stems will retain a natural life-like appearance and shape. In general a preservative must also act as a humectant. This is essential to prevent dry out of foliage with subsequent curling and poor apperance when humidity conditions are low.

The alkylene oxide oligomers are selected from di- and polyethylene glycols and di- and polypropylene glycols. The former have the general formula $H(OCH_2CH_2)_mOH$ where m is 2-35 and the molecular weight is in the range of about 106 to 1558. The latter compositions have the general formula $H(OCHCH_3CH_2)_nOH$ where n is 2-8 and the molecular weight falls in the range of about 134 to 482. Preferred materials are polyethylene glycols having an average molecular weight of about 200 to 1000 and polypropylene glycols having an average molecular weight below about 450.

The method is practiced by perfusing the aqueous treatment solution into the vascular system of the plant. This is done by placing the freshly exposed xylem of a stem into the aqueous preservative composition. The plant and preservative composition are held at a temperature in the range of about 20°-50° C., at a relative humidity in the range of about 20% to 80%, for a period of time up to about 14 days. In the usual practice of the method the xylem is exposed in a generally transversely cut stem. However, it may also be exposed by making cuts through the bark of the stem of a still rooted plant without fully girdling the stem. A sealed collar and associated liquid supply source is placed around the stem so that the cuts are exposed to the preservative solution.

The total concentration of primary and secondary humectant materials, if the latter are present, in the preservative solution is about 2-60% by weight while the secondary humectant may be present up to about half of the total weight of humectant/preservative materials. It most preferably is present in a concentration lower than about 25% by weight of the concentration of primary humectant. Stated otherwise, in the preferred compositions the secondary humectant would comprise not more than about one fifth to one fourth of the total humectant/preservative materials present in the treating solution.

It is an object of the present invention to provide a method of preserving plants or portions of plants which reduces the bleeding of preservative materials.

It is another object to use new chemical materials to achieve preserved plants having high quality and resistance to bleeding.

It is a further object to provide preserved plants which are resistant to bleeding.

These and many other objects will become readily apparent to those reading the detailed description taken in conjunction with the drawings.

DETAILED DESCRIPTION OF THE INVENTION

As the present inventors have noted before, bleeding of treatment chemicals is a serious problem after high humidity exposure of conventionally treated preserved plants. In those preserved plants which have been of sufficiently high quality for successful commercial sale, glycerine has almost universally been the preservative material employed.

Many species of preserved plant materials are now available for decorative uses. These range from small trees up to about 7 meters in height down to smaller plants which are used in floral arrangements. Of the tree sized plants, palms are of particular commercial significance with two species having primary importance.

Figure 1:
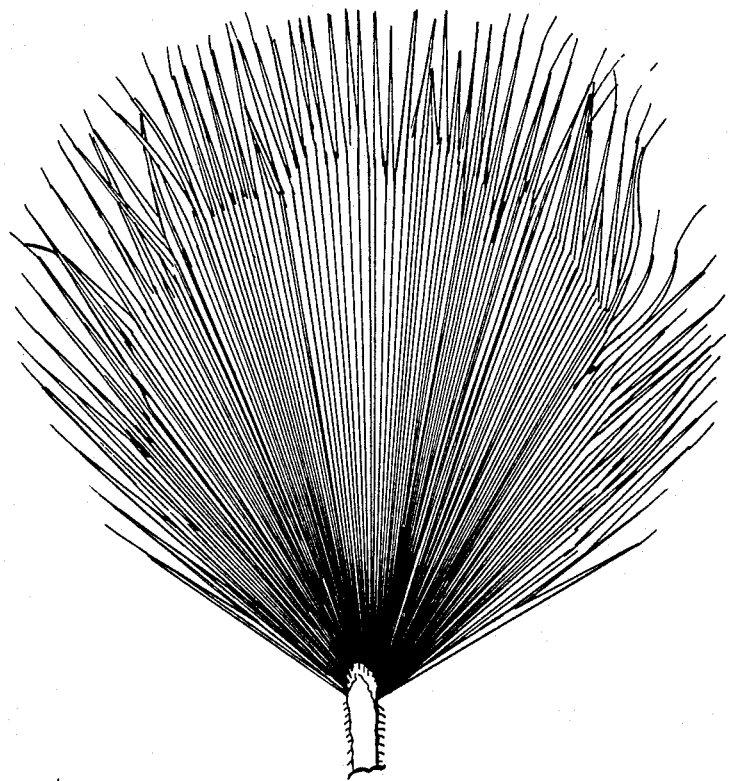
FIG. 1 shows a palm fan treated with a glycerine-based preservative solution.
Figure 3:
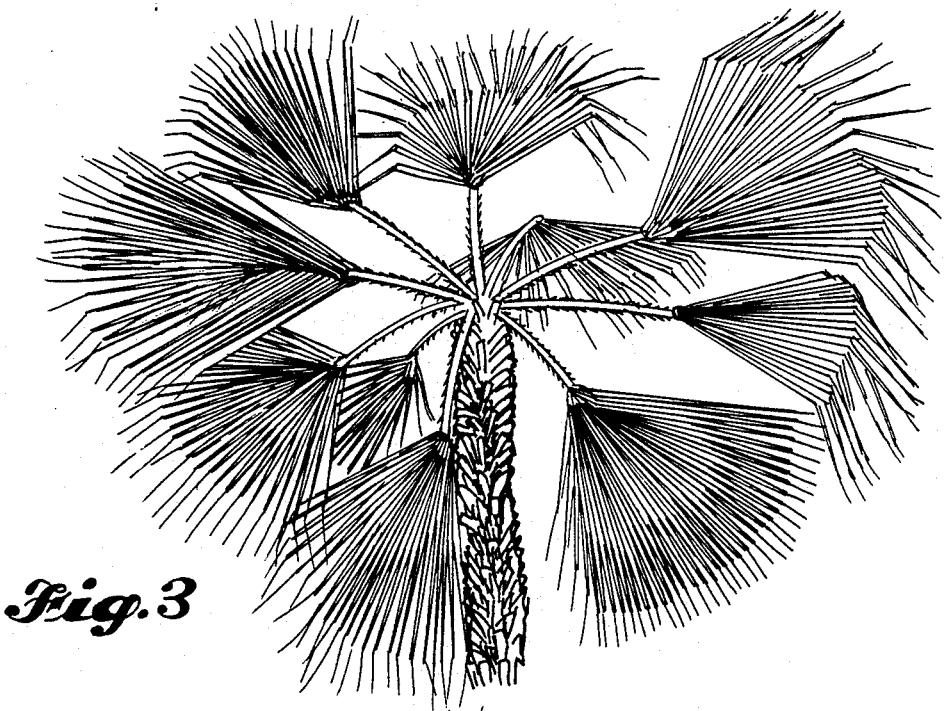
FIG. 3 is an elevation view of a Washingtonia palm preserved with a glycerine-based material and shwong a typical leaf droop.

These are *Pheonix canariensis*, the Canary Island date palm and *Washingtonia robusta*, a representative of the fan palms. In addition to the problem of bleeding, a second problem has arisen with these species. The normal treatment with glycerine gives a relatively limp stem or petiole so that over time the leaves tend to droop and ultimately become fixed in drooped position. A second problem is that the leaves of the glycerine teated fan palms frequently do not open to their broadest extent. These conditions are represented in FIGS. 1 and 3 which are ink drawings make from actual photographs.

Figure 2:
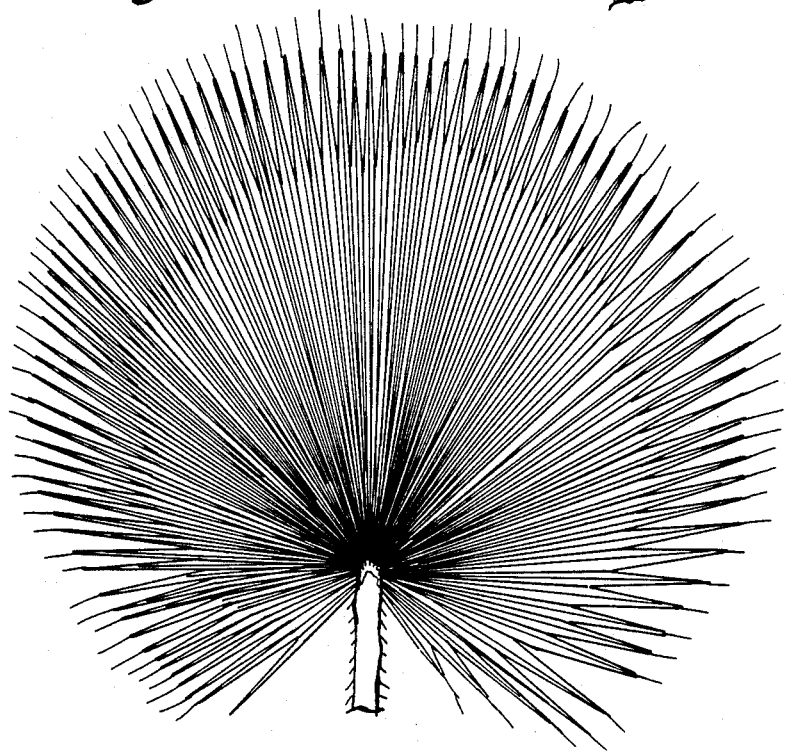
FIG. 2 shows a palm fan similarly treated with a tripropylene glycol-based preservative solution.
Figure 4:
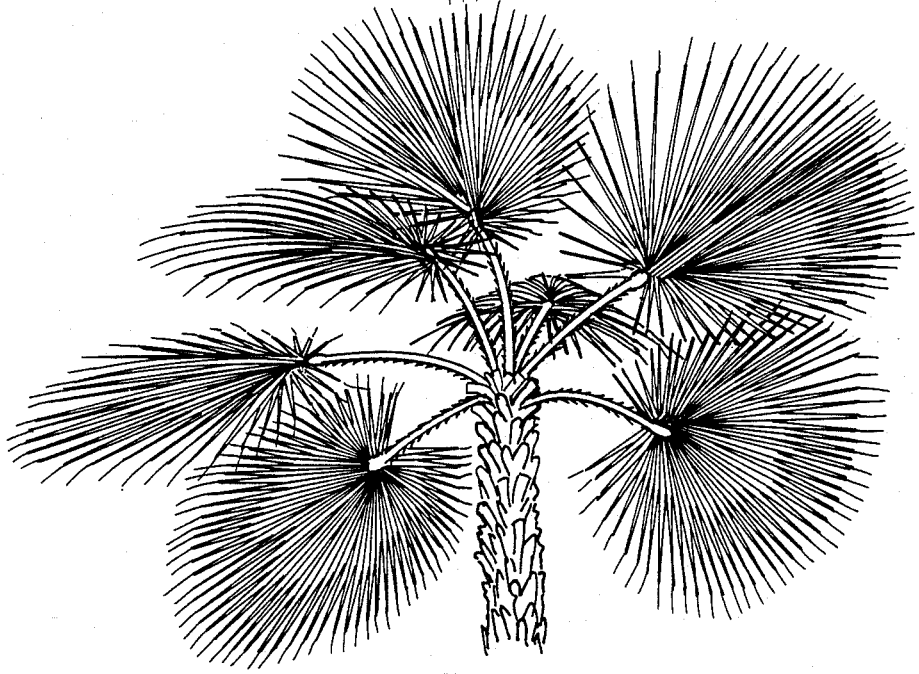
FIG. 4 is a view similar to FIG. 3 showing a Washingtonia palm treated with preservative based on tripropylene glycol.

Quite surprisingly the above problem of leaf droop has been solved using any of the humectant preservative materials of the present invention. FIGS. 2 and 4 shown Washingtonia palm treated using tripropylene glycol as the preservative material. Note in FIG. 2. that the fan has remained open to its widest extent and in FIG. 4 that the petioles remain straight and the leaves or fans are in their normal position. This advantage was entirely unexpected and the reasons for it are not fully understood.

The following examples will teach the best most presently known to the inventors of practicing the method of their invention.

EXAMPLE 1

A standard preservation solution was made up as follows:

| Humectant | 30.00% by weight |
| --- | --- |
| Water | 69.28 |
| Potassium nitrate | 0.555 |
| Citric acid | 0.0083 |
| C.I. Acid red No. 52* | 0.152 |
| Biocide | Trace |

*C.I. No. 45100

This red treatment solution was chosen for test purposes since untreated portions of the plants are more readily apparent than is the case with the more usual blue-green dyes.

Plants to be treated were severed from the roots and the cut ends placed in the solution for 3-14 days, at a solution and environment temperature of 20°-45° C. and a relative humidity normally 60% or under. However, deviations from all of these conditions were occasionally made, as will be noted in the following examples. Where humectant concentration was varied above or below 30% an equivalent amount of water was removed or added to keep the combined amount of humectant plus water constant.

Treatment conditions were adjusted depending on the species and variety of plant and the growth stage or season in which it was treated. There is great variation both within and between species and no single set of conditions or composition of treating solution is always ideal for any given variety. Treatment conditions must usually be adjusted based on past experience and trial runs. Some plant species do not respond at all satisfactorily to preservative treatments. Others may respond well at some seasons and not at others. In general, the best quality is achieved when the plant being treated is in a season of active growth.

Following treatment with the perservative solution the plants were normally conditioned for 2-3 days at 20°-22° C. and about 50-65% R.H. before further evaluation.

The quality of treated plants is ranked on an arbitrary scale of 1-5 based on appearance and ultimate marketability. This scale is as follows:

| Rating | Description | Salable |
| --- | --- | --- |
| 5 | Well treated, good color and uniformity | Yes |
| 4 | Well treated, slight nonuniformity | Yes |
| 3 | Mostly treated, mottled, slightly dry | Questionable |
| 2 | Dye in and adjacent to midveins only, foliage mostly dry | No |
| 1 | Untreated, dry foliage | No |

By well treated is meant that the treatment solution has been taken up uniformly to the edges and tips of the foliage, as indicated by dye distribution, and the foliage is generally soft, supple, and of natural feel and appearance, except perhaps for color.

Conditioned plants were then tested for bleed resistance by placing them in an environmental chamber at 90% R.H. and 21° C. for 14 days. Samples were checked daily for visible bleeding at several sites. These included young or immature stems, mature stems, leaves, flowers and any cut or abraded stem areas. Almost invariably bleeding would first occur at cut or abraded areas then, most usually, from young or immature stem portions of the plants.

The following plant species were the subject of preservation tests: *Eucalyptus gunnii*, *Gypsophilia paniculata* (baby's breath), *Limonium sinuata* (statice), *Fagus sylvatica* (European beech), *Juniperis chinensis* cv. Bluepoint, *Mahonia aquifolium* (Oregon grape), *Gaultherica shallon* (salal), *Pheonix canaeriensis* (Canary Island date palm), and *Washingtonia robusta* (fan palm). Hereafter these plants are generally referred to only by genus; i.e., "Limonium" should be considered to always mean *Limonium sinuata*. All of these plants are commercially important species in the preserved ornamental plant trade.

EXAMPLE 2

As noted earlier, the principal function of a preservative/humectant is to replace, at least in part, the water normally present in the plant tissues with a material of low volatility. This preservative must also be at least somewhat hygroscopic to prevent dry out at low humidity with resulting curling and poor appearance, especially of the leaves of broadleaf species. Glycerine has been used almost universally in the past as the preservative material of commercial interest. Its effectiveness has been so well known there has been little effort or incentive to look for other materials that might serve as well or better.

The present inventors have determined that bleeding at high humidities is caused by the hygroscopic nature of the humectant/preservative material. It is a characteristic of hygroscopic materials that they continue over time to take up moisture and asymptotically approach some limiting amount. This amount is dependent on the material itself and the temperature and relative humidity of the ambient environment. Thus, rate and amount of water pickup is relatively high initially but continually decreases over time. Bleeding will not occur as long as there is some unfilled void volume remaining in the treated plant. If, however, the void spaces become filled with liquid, water pickup still continues. There is no place within the plant structure to accommodate this extra volume of liquid and bleeding occurs through leaf stomata or other available openings.

The present inventors have investigated a large number of potential compounds for their stability as (1) preservative/humectants and (2) the contribution they make to the bleeding problem. A first screening test was to expose open dishes of each material to a 90% R.H., 21° C. atmosphere for extended periods of time. Weight gain was measured periodically during the test period.

Materials tested and the weight gain results are shown in Table I.

varying conditions designed to give a wide range of ultimate glycerine uptake. Preservative uptake is based on grams of preservative per 100 g of fresh plant weight. This is calculated from the measured solution uptake multiplied by solution density and concentration of humectant/preservative in the solution. Where a concentration other than 30% glycerine (or other humectant) was used, an appropriate adjustment was made by increasing or decreasing the amount of water in treating solution.

Results of the tests are given in Table II.

TABLE II

| | | Glycerine-Based Preservatives | | | | | | |
|---|---|---|---|---|---|---|---|---|
| Sample No. | Species | Preservative Conc., % | Treatment Conditions | | | Uptake g/100 g | Quality Rating | Bleed Time Days |
| | | | Time, hr. | Temp., °C. | R.H., % | | | |
| 1 | Eucalyptus | 30 | 261 | 21 | 65 | 47 | 5 | 1 |
| 2 | Eucalyptus | 20 | 261 | 21 | 65 | 37 | 5 | 1 |
| 3 | Eucalyptus | 10 | 260 | 21 | 65 | 51 | 5 | 1 |
| 4 | Eucalyptus | 5 | 260 | 21 | 65 | 21 | 5 | 1 |
| 5 | Eucalyptus | 2 | 260 | 21 | 65 | 10 | 5 | 5 |
| 6 | Gypsophilia | 50 | 65 | 40 | 60 | 40 | 5 | 1* |
| 7 | Gypsophilia | 40 | 65 | 40 | 60 | 41 | 5 | 1* |
| 8 | Gypsophilia | 30 | 65 | 40 | 60 | 40 | 5 | 1* |
| 9 | Gypsophilia | 20 | 65 | 40 | 60 | 35 | 5 | 1* |
| 10 | Gypsophilia | 10 | 65 | 40 | 60 | 25 | 5 | 1* |
| 11 | Phoenix | 30 | 213 | 21 | 60 | 20 | 3–4 | 1–5 |
| 12 | Fagus | 30 | 214 | 21 | 60 | 29 | 5 | 1 |
| 13 | Juniperis | 30 | 214 | 21 | 60 | 25 | 4–5 | 3 |

*Severe bleeding

TABLE I

| | % Weight Gain at 21° C. and 90% R.H. after Various Times, Hours | | | | | | |
|---|---|---|---|---|---|---|---|
| Sample Material | 7 | 24 | 48 | 72 | 144 | 204 | 408 |
| Glycerol | 10 | 26 | 41 | 53 | 80 | 102 | 129 |
| Polyethylene glycol 200 | 10 | 24 | 38 | 47 | 68 | 84 | 102 |
| Polyethylene glycol 400 | 12 | 24 | 32 | 39 | 54 | 67 | 82 |
| Polyethylene glycol 600* | 9 | 19 | 28 | 36 | 52 | 67 | 83 |
| Polyethylene glycol 1000* | 5 | 13 | 22 | 29 | 46 | 60 | 75 |
| Polyethylene glycol 3250 | 2 | 4 | 6 | 7 | 9 | 13 | 23 |
| Dipropylene glycol | 13 | 27 | 37 | 43 | 56 | 69 | 85 |
| Tripropylene glycol* | 12 | 23 | 30 | 35 | 44 | 52 | 63 |
| 1,3-butanediol | 15 | 31 | 42 | 49 | 66 | 81 | 101 |
| 95% TPG-5% glycerol | 11 | 22 | 31 | 37 | 50 | 62 | 82 |
| 30% TPG-70% glycerol | 12 | 25 | 35 | 43 | 57 | 69 | 87 |
| 70% PEG 600-30% glycerol | 10 | 23 | 35 | 44 | 65 | 80 | 97 |
| 50% PEG 600-50% glycerol | 10 | 23 | 36 | 45 | 66 | 83 | 103 |
| 70% PEG 1000-30% glycerol | 7 | 18 | 29 | 37 | 56 | 71 | 88 |
| 50% PEG 1000-50% glycerol | 7 | 18 | 33 | 45 | — | 91 | 111 |
| 50% TPG-50 PEG 600 | 11 | 24 | 35 | 43 | 57 | 69 | 85 |

*Results for PEG 600 and 1000 are averages from three trials. Those for TPG are averages from two trials.

Of all the materials tested, glycerol showed the highest weight gain over time. Mixtures of glycerol with less hygroscopic compounds showed intermediate results roughly proportional to the percentages of the individual components.

EXAMPLE 3

To demonstrate the bleeding propensity of a glycerine based preservative, five species were treated using varying conditions designed to give a wide range of ultimate glycerine uptake.

Only in the case of sample No. 5, where glycerine takeup was very low, did bleed resistance exceed four days. Four days is considered to be a desirable minimum time for freedom from bleeding. This corresponds to the time an office building might be without air conditioning over a long holiday weekend. Humidity and/or temperature could rise to values well above normal under such conditions.

EXAMPLE 4

The first group of new materials to be tested as potential low bleeding preservatives, from those screened in Example 2, were polyethylene glycols (PEG) having a range of average molecular weights. These materials have the formula $H(OCH_2CH_2)_mOH$ where m is 2–35. Among the materials tested the following relationship exists:

| Average M.W. | m (Approximately) |
|---|---|
| 200 | 4 |
| 400 | 9 |
| 600 | 13 |
| 1000 | 22 |
| 1450 | 32.5 |
| 2000 | 45 |
| 3250 | 73.5 |

Test results using perservation treatment solutions, all having 30% PEG, are given in Table III.

TABLE III

| | | Polyethylene Glycol-Based Preservatives | | | | | | | |
|---|---|---|---|---|---|---|---|---|---|
| Sample No. | Species | Preservative | | Treatment Conditions | | | Uptake g/100 g | Quality Rating | Bleed Time Days |
| | | Material | Conc., % | Time, hr. | Temp., °C. | R.H., % | | | |
| 14 | Eucalyptus | PEG 200 | 30 | 215 | 21 | 65 | — | <5 | 4–5 |
| 15 | Eucalyptus | PEG 400 | 30 | 215 | 21 | 65 | — | <5 | >14 |
| 16 | Eucalyptus | PEG 600 | 30 | 215 | 21 | 65 | — | <5 | >14 |
| 17 | Eucalyptus | PEG 1000 | 30 | 215 | 21 | 65 | — | 3–4 | >14 |
| 18 | Eucalyptus | PEG 1450 | 30 | 215 | 21 | 65 | — | 4 | 3–8 |
| 19 | Eucalyptus | PEG 2000 | 30 | 215 | 21 | 65 | — | 3 | >14 |

TABLE III-continued

| Sample No. | Species | Polyethylene Glycol-Based Preservatives | | | | | Uptake g/100 g | Quality Rating | Bleed Time Days |
|---|---|---|---|---|---|---|---|---|---|
| | | Preservative | | Treatment Conditions | | | | | |
| | | Material | Conc., % | Time, hr. | Temp., °C. | R.H., % | | | |
| 20 | Eucalyptus | PEG 3250 | 30 | 215 | 21 | 65 | — | 2 | >14 |
| 21 | Limonium | PEG 400 | 30 | 91 | 40 | 60 | 21 | 5 | 1 |
| 22 | Washingtonia | PEG 200 | 30 | — | 40 | 60 | 35 | 5 | 1–4 |
| 23 | Gypsophilia | PEG 400 | 30 | 65 | 40 | 60 | 21 | 3 | <1 |

Bleed results improve; i.e., bleeding tendency decreases, with increasing average molecular weight of the PEG. Conversely, quality appears to be poorer as molecular weight increases. Satisfactory quality was not obtained with PEG having a molecular weight greater than about 1450. Apparently the larger aliphatic dihydroxy polyether molecules are too large to effectively diffuse uniformly through the plant tissue.

The three species represented by Sample Nos. 21–23 did not have good bleed resistance under the conditions used. This points up what was noted before. Not all preservation treatments will work well for all species at all times during the seasonal periods.

Blends of various PEG materials were made with glycerine. In no case did the amount of glycerine exceed more than 1/6 of the active perservative/humectant materials. Treating solution compositions, conditions, and results are given in Table IV.

The preferred polyethylene glycol oligomers have from 2–35 [OCH$_2$CH$_2$] units, corresponding to average molecular weights in the range of about 100–1600. The most preferred materials are in the average molecular weight range of 400–1200.

In general, satisfactory quality and fair to excellent bleed resistance was obtained in all samples tested, with the exception of Nos. 27 and 28. These two samples were made using PEG having molecular weights above the desired range. It is believed that ethylene or propylene glycol could be substituted in whole or part for glycerine.

EXAMPLE 5

Tripropylene glycol (TPG) has been found to be an excellent preservative material, combining the attributes of good product quality with generally excellent bleed resistance. Tests were run using five plant species with various TPG concentrations and treatment conditions. These conditions and the results obtained are given in Table V.

TABLE V

| Sample No. | Species | Di- and Tripropylene Glycol-Based Preservatives | | | | Uptake g/100 g | Quality Rating | Bleed Time Days |
|---|---|---|---|---|---|---|---|---|
| | | Preservative Conc., % | Treatment Conditions | | | | | |
| | | | Time, hr. | Temp., °C. | R.H., % | | | |
| 35 | Eucalyptus | 20 | 259 | 21 | 65 | 23 | 3–4 | 3 |
| 36 | Eucalyptus | 10 | 259 | 21 | 65 | 20 | 4 | 2 |
| 37 | Juniperis | 30 | 259 | 21 | 65 | 21 | 4 | >14 |
| 38 | Juniperis | 50 | 66 | 40 | 60 | 26 | 5 | 1–7 |
| 39 | Juniperis | 40 | 66 | 40 | 60 | 22 | 5 | 7 |
| 40 | Juniperis | 30 | 66 | 40 | 60 | 18 | 5 | 7 |
| 41 | Juniperis | 20 | 66 | 40 | 60 | 12 | 5 | >14 |
| 42 | Juniperis | 10 | 66 | 40 | 60 | 8 | 5 | >14 |
| 43 | Gypsophilia | 30 | 65 | 40 | 60 | 19 | 4 | 2 |
| 44 | Gypsophilia | 20 | 65 | 40 | 60 | 17 | 5 | 2 |
| 45 | Gypsophilia | 10 | 65 | 40 | 60 | 11 | 5 | 2 |
| 46 | Phoenix | 30 | 68 | 40 | 60 | 20 | 5 | 13 |
| 47 | Phoenix | 20 | 68 | 40 | 60 | 14 | 5 | >14 |
| 48 | Mahonia | 20 | 143 | 30 | 60 | 14 | 4 | >14 |
| 49 | Mahonia | 10 | 143 | 30 | 60 | 9 | 4 | >14 |
| 50 | Eucalyptus | 30* | 215 | 21 | 65 | — | 3 | >14 |

*Dipropylene glycol substituted for tripropylene glycol.

Interestingly, as seen here and in the other examples, even low concentrations of preservative/humectant in the treating solution and the plant itself can give excellent product quality. The bleed resistance is frequently improved as well as is seen here in Sample Nos. 41 and 42. It can be stated as a generalization that the minimum amount of material necessary for good perservation

TABLE IV

| Sample No. | Species | Polyethylene Glycol/Glycerine-Based Preservatives | | | | | | Quality Rating | Bleed Time Days |
|---|---|---|---|---|---|---|---|---|---|
| | | PEG | | Glycerine | Treatment Conditions | | | | |
| | | Type | % | % | Time, hr. | Temp., °C. | R.H., % | | |
| 24 | Eucalyptus | 600 | 25 | 5 | 215 | 21 | 65 | 4 | 3–7 |
| 25 | Eucalyptus | 1000 | 25 | 5 | 215 | 21 | 65 | 4 | 3–4 |
| 26 | Eucalyptus | 1450 | 25 | 5 | 215 | 21 | 65 | 4 | 3–13 |
| 27 | Eucalyptus | 2000 | 25 | 5 | 214 | 21 | 65 | 3 | >14 |
| 28 | Eucalyptus | 3250 | 25 | 5 | 214 | 21 | 65 | 2 | >14 |
| 29 | Eucalyptus | 1000 | 25 | 5 | 214 | 21 | 65 | 4 | 5–6 |
| 30 | Eucalyptus | 1000 | 26 | 4 | 214 | 21 | 65 | 4 | 6–8 |
| 31 | Eucalyptus | 1000 | 27 | 3 | 214 | 21 | 65 | 4–5 | 4–9 |
| 32 | Eucalyptus | 1000 | 28 | 2 | 214 | 21 | 65 | 4 | 7–8 |
| 33 | Eucalyptus | 1000 | 29 | 1 | 214 | 21 | 65 | 4 | 2–7 |
| 34 | Eucalyptus | 1000 | 30 | 0 | 214 | 21 | 65 | 4 | 2–9 | should be used where bleed resistance is of concern. Again, this relates to maximizing the void volume in the plant tissue available for holding moisture taken from the air during high humidity conditions.

It might be noted that the Gypsophilia is a species particularly prone to bleeding under even the best known treatment conditions. The two days to bleeding in sample Nos. 43-45 should be compared with the severe bleeding in less than one day (sample Nos. 6-10) using glycerine treatment. The present results, while not as good as desired, represent a very significant improvement.

Dipropylene glycol, used on only sample No. 50, gave excellent bleed resistance but only fair quality. This material would be expected to perform in generally equivalent fashion to TPG when used with other species.

The molecular weight range of propylene oligomers that will give satisfactory quality appears to be narrower than for ethylene oxide oligomers. The general formula for these compounds is $H(OCHCH_3CH_2)_nOH$ where n is 2-8. This corresponds to average molecular weights in the range of about 130-500.

EXAMPLE 6

Two butanediols have been used as preservative materials with generally very good to excellent quality and good resistance to bleeding. 1,3- and 1,4-butanediol appear to be about equivalent to each other. Conditions of treatment and results are seen in Tables VI and VII.

TABLE VI 1,3-Butanediol-Based Preservatives

| Sample No. | Species | Preservative Conc., % | Treatment Conditions Time, hr. | Temp., °C. | R.H., % | Uptake g/100 g | Quality Rating | Bleed Time Days |
|---|---|---|---|---|---|---|---|---|
| 51 | Mahonia | 50 | 65 | 40 | 60 | 24 | 4 | 2 |
| 52 | Mahonia | 40 | 65 | 40 | 60 | 23 | 4 | 2 |
| 53 | Mahonia | 30 | 65 | 40 | 60 | 18 | 5 | 2 |
| 54 | Mahonia | 20 | 65 | 40 | 60 | 15 | 5 | >14 |
| 55 | Mahonia | 10 | 30 | 40 | 60 | 12 | 5 | >14 |
| 56 | Gypsophilia | 30 | 65 | 40 | 60 | 14 | 4 | 2 |
| 57 | Gypsophilia | 20 | 65 | 40 | 60 | 14 | 4 | 1 |
| 58 | Gypsophilia | 10 | 65 | 40 | 60 | 9 | 4 | 4->14 |
| 59 | Limonium | 30 | 65 | 40 | 60 | 17 | 5 | 2 |
| 60 | Limonium | 20 | 65 | 40 | 60 | 14 | 5 | 7->14 |
| 61 | Limonium | 10 | 65 | 40 | 60 | 9 | 5 | >14 |
| 62 | Gaultheria | 30 | 65 | 40 | 60 | 13 | 2 | >14 |
| 63 | Gaultheria | 20 | 65 | 40 | 60 | 11 | 3 | >14 |
| 64 | Gaultheria | 10 | 65 | 40 | 60 | 10 | 5 | >14 |
| 65 | Washingtonia | 30 | — | 40 | 60 | 34 | 5 | >14 |

TABLE VII 1,4-Butanediol-Based Preservatives

| Sample No. | Species | Preservative Conc., % | Treatment Conditions Time, hr. | Temp., °C. | R.H., % | Uptake g/100 g | Quality Rating | Bleed Time Days |
|---|---|---|---|---|---|---|---|---|
| 66 | Mahonia | 50 | 142 | 30 | 60 | 23 | 3 | 1 |
| 67 | Mahonia | 40 | 142 | 30 | 60 | 23 | 4 | 1 |
| 68 | Mahonia | 30 | 142 | 30 | 60 | 21 | 5 | 1 |
| 69 | Mahonia | 20 | 142 | 30 | 60 | 18 | 5 | 1 |
| 70 | Mahonia | 10 | 142 | 30 | 60 | 12 | 5 | 1 |
| 71 | Gaultheria | 50 | 142 | 30 | 60 | 20 | 2 | >14 |
| 72 | Gaultheria | 40 | 142 | 30 | 60 | 17 | 2 | >14 |
| 73 | Gaultheria | 30 | 141 | 30 | 60 | — | 2.5 | >14 |
| 74 | Gaultheria | 20 | 142 | 30 | 60 | 17 | 3 | >14 |
| 75 | Gaultheria | 10 | 141 | 30 | 60 | — | 5 | >14 |

Once again, the ue of low concentratons of humectant/preservative in the treating solutions result in plants showing good quality with superior bleed resistance. This is especially evident in sample Nos. 54, 55, 58, 60 and 61 treated with 1,3-butanediol. Note sample Nos. 64, 68-70 and 75 where product quality was also improved by the use of lower concentrations.

EXAMPLE 7

In U.S. patent application, Ser. No. 113,312, filed Oct. 28, 1987, and commonly owned by the present assignee, a number of materials are disclosed that contribute flame retardancy to preserved plants. These flame retardant materials are generally used in combination with glycerine but two groups of them serve as effective preservatives in their own right. These are water soluble cyclic phosphonate esters and magnesium chloride and bromide hexahydrate. Surprisingly, the phosphonate esters especially also confer reduced bleeding used either by themselves or as a minor ingredient in combination with the polyols just described.

The water soluble phosphonate esters are generally prepared by reacting alkyl-halogen free esters with a bicyclic phosphite. Examples of suitable materials are as follows:

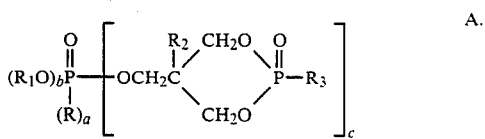

A.

where a is 0, 1, or 2, b is 0, 1, or 2, C is 1, 2, or 3 and a+b+c is 3; R and $R_1$ are alkyl, alkoxy, aryl, aryloxy, alkaryl, alkaryloxy, aralkyl, aryloxy-alkoxy, or aralkoxy wherein the alkyl portion of these groups may contain hydroxyl but not halogen and the aryl portion may contain chlorine, bromine and hydroxyl groups;

$R_2$ Is alkyl, hydroxy-alkyl, or aryl; $R_3$ is lower alkyl ($C_1$-$C_4$) or hydroxyalkyl ($C_1$-$C_4$);

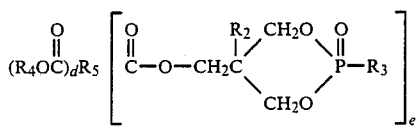  B.

where d is 0, 1, or 2; e is 1, 2, or 3; d+e is 3; $R_2$ is as defined above, $R_3$ is as defined above, $R_4$ is alkyl, aryl, alkaryl, aralkyl, or aryloxyalkyl, wherein the aryl portion may contain bromine, chlorine or hydroxyl; and $R_5$ is monovalent, divalent or tervalent alkyl, alkylene, aryl, or arylene radical wherein the aryl or arylene radical may contain bromine, chlorine, alkyl or hydroxy groups; and

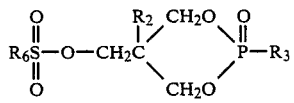  C.

where $R_2$ and $R_3$ are as defined above; and $R_6$ is alkyl, aryl, alkylaryl, or arylakyl wherein the aryl portion may contain bromine, chlorine or hydroxyl.

Preparation of these materials is described in Anderson et al, U.S. Pat. No. 3,789,091.

A preferred material is defined by formula A wherein a is 1, bis 0 or 1, and c is 2-b; R, $R_1$, and $R_3$ are methyl and $R_2$ is ethyl. This is shown by the formula.

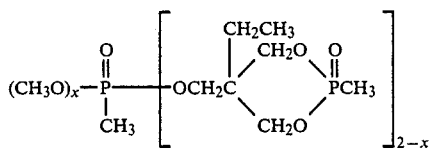  D.

where x is 0 or 1.

The preferred composition is available as Antiblaze 19 or Antiblaze 19T from Albright and Wilson, Inc., Richmond, Va. Antiblaze is a registered trademark of the above supplier.

Mixtures of tripropylene glycol and magnesium chloride hexahydrate were made for a preservation solution. The $MgCl_2.6H_2O$ was present as either 25% or 33% of the active preservative/humectant material. Six plant speices were treated is outlined in Table VIII.

Quality and bleed resistance could generally be characterized as fair to excellent. As has been observed before, the quality of some species was superior to others treated in exactly the same manner.

In sample No. 84 1,3-butanediol was substituted for tripropylene glycol.

The inventors have herein been disclosed the best mode or modes known to them of practicing their invention. They wish to emphasize again the great variability that is to be found and expected when dealing with natural materials as diverse as living plants. Any particular set of treatment conditions or materials will not be optimum for all species, nor even for any given species, at different times of the growing season.

Since many features of the invention other than those disclosed above will be apparent to those skilled in the art, the invention is to be considered limited only as it is defined by the following claims.

We claim:

1. A method of preserving plants which achieves reduced exudation of preservative materials when said preserved plants are subjected to elevated humidity conditions which comprises:

perfusing into living plants an aqueous preservative composition containing a sufficient amount of a primary hydrophilic humectant material selected from alkylene oxide oligomers, 1,3-butanediol, 1,4-butanediol, and mixtures thereof with each other and with minor amounts of a secondary humectant material selected from glycerol, ethylene glycol, propylene glycol, $MgCl_2 \cdot 6H_2O$, $MgBr_2 \cdot 6H_2O$, and water soluble cyclic phosphonate esters.

2. The method of claim 1 in which the alkylene oxide oligomers are selected from di- and polyethylene glycols having the formula $H(OCH_2CH_2)_mOH$ where m is 2-35 and the average molecular weight is in the range of about 106 to 1558, and dipropylene and polypropylene glycols of the formula $H(OCHCH_3CH_2)_nOH$ where n is 2-8 and the average molecular weight falls in the range of about 134 to 482.

3. The method of claim 2 in which the primary humectant is a polyethylene glycol having an average molecular weight of about 200-1000.

4. The method of claim 2 in which the primary humectant is a polypropylene glycol having an average molecular weight up to about 450.

5. The method of claim 4 in which the primary humectant is tripropylene glycol.

6. The method of claim 1 where the primary humectant is 1,3- or 1,4-butanediol.

7. The method of claim 1 in which the preservative is perfused into the vascular system of the plant by placing the freshly exposed xylem of a stem into the aqueous preservative composition and maintaining the plant and preservative composition at a temperature in the range

TABLE VIII

| | | Tripropylene Glycol/Magnesium Chloride-Based Preservatives | | | | | | | |
|---|---|---|---|---|---|---|---|---|---|
| Sample | | Preservative Conc., % | | Treatment Conditions | | | Uptake | Quality | Bleed Time |
| No. | Species | TPG | $MgCl_2.6H_2O$ | Time, hr. | Temp., °C. | R.H., % | g/100 g | Rating | Days |
| 76 | Phoenix | 30 | 10 | 259 | 21 | 65 | 18 | 5 | 5->14 |
| 77 | Fagus | 30 | 10 | 259 | 21 | 65 | 19 | 3 | >14 |
| 78 | Juniperis | 30 | 10 | 259 | 21 | 65 | 16 | 4 | 5 |
| 79 | Eucalyptus | 30 | 10 | 259 | 33 | 65 | 32 | 3 | 1-7 |
| 80 | Phoenix | 20 | 10 | 188 | 24 | 60 | 16 | 3 | >8 |
| 81 | Phoenix | 20 | 10 | 189 | 30 | 60 | 21 | 4 | 7 |
| 82 | Phoenix | 20 | 10 | 189 | 40 | 60 | 28 | 5 | 2 |
| 83 | Limonium | 30 | 10 | 117 | 24 | 60 | 14 | 3 | 3 |
| 84 | Washingtonia | 30* | 10 | — | 40 | 60 | 31 | 5 | 1-3 |

*1,3 butanediol substituted for tripropylene glycol.

of about 20°–50° C. at a relative humidity in the range of about 20%–80% for a period of time up to about 14 days.

8. The method of claim 7 in which the xylem is exposed in a generally transversely cut stem.

9. The method of claim 7 in which the xylem is exposed by making cuts through the bark of the stem of a still rooted plant without fully girdling the stem and perfusing the preservative into the plant through the cuts.

10. The method of claim 1 in which the combined primary and secondary humectant materials are present in the preservative solution in a concentration of about 2–60% by weight.

11. The method of claim 7 in which the combined primary and secondary humectant materials are present in the preservative solution in a concentration of about 2–60% by weight.

12. The method of claim 10 in which the secondary humectant, if present, is in a concentration lower than the concentration of primary humectant mataerial.

13. The method of claim 12 in which the secondary humectant, if present, is in an amount lower than about 25% by weight of the concentration of primary humectant.

14. A plant preserved by the method of claim 1.

* * * * *